United States Patent [19]

Busse et al.

[11] 4,447,440

[45] May 8, 1984

[54] SULPHENAMIDES-CONTAINING LIPOXYGENASE INHIBITING AGENTS AND THEIR USE IN PHARMACEUTICAL COMPOSITIONS

[75] Inventors: Wolf-Dieter Busse, Wuppertal; Edmund Krauthausen, Cologne; Mithat Mardin, Wuppertal, all of Fed. Rep. of Germany

[73] Assignee: Bayer Aktiengesellschaft, Leverkusen, Fed. Rep. of Germany

[21] Appl. No.: 368,193

[22] Filed: Apr. 14, 1982

[30] Foreign Application Priority Data

May 7, 1981 [DE] Fed. Rep. of Germany ....... 3118126

[51] Int. Cl.³ .............................................. A61K 31/41
[52] U.S. Cl. .................................................... 424/269
[58] Field of Search ........................................ 424/269

*Primary Examiner*—Stanley J. Friedman
*Attorney, Agent, or Firm*—Sprung, Horn, Kramer & Woods

[57] ABSTRACT

The invention relates to sulphenamide compounds of Formula (I) as defined herein and to methods for their preparation. Also included in the invention are compositions containing said sulphenamide compounds; and the use of said compounds and compositions as lipoxygenase inhibiting agent.

12 Claims, No Drawings

SULPHENAMIDES-CONTAINING LIPOXYGENASE INHIBITING AGENTS AND THEIR USE IN PHARMACEUTICAL COMPOSITIONS

The present invention relates to the use as lipoxygenase inhibiting agents of sulphenamides, some of which are known.

Some of the sulhenamides used according to the invention are already known in the rubber industry as vulcanisation retarders (see U.S. Pat. Nos. 3,546,185, 3,562,225, 3,586,696, 3,645,987, 3,689,467, 3,725,361, 3,862,051, 3,872,061, 3,915,940, 3,993,633, 4,156,680 and 4,207,216, British Patent Specification 1,345,144 and German Offenlegungsschriften (DOS) (German Published Specifications) Nos. 1,620,822, 1,913,725, 2,117,615, 2,136,066, 2,136,090, 2,142,648, 2,164,810, 2,305,555, 2,314,838, 2,337,642 and 2,339,986).

It is also known that the metabolites of arachidonic acid which are formed by the enzyme lipoxygenase, are involved in the development of inflammatory and allergic processes (see E. J. Goetzl, Immunology 40, 709–719 (1980); Ford-Hutchinson et al., J. Pharm Pharmacol. 32, 517 (1980) and Nature 286, 264 (1980) and Samuelsson, Trends in Pharmacol. Sci., May 1980, 227, Borgeat et al., J. Med. Chem. 24, 121 (1981)).

Known inhibitors of lipoxygenase such as nordihydroguaiaretic acid, 3-amino-1-(3-trifluoromethylphenyl)pyrazoline, phenidone and 5,8,11,14-eicosatetrainoic acid are either simultaneously active as inhibitors of cyclooxygenase, or only active at very high concentrations. The inhibition of the enzyme cyclooxygenase of the metabolism of arachidonic acid leads to a global inhibition of the synthesis of prostaglandins and to a stimulation of the lipoxygenase route, which causes gastrotoxicity or pro-inflammatory and asthmatic effects (see S. S. Yen and W. Kreutner, Agents and Actions, 10, 274 (1980) and G. J. Blackwell and R. J. Flower, Prostaglandins 16, 417 (1978); and see also Brune et al., J. Pharm. Pharmacol. 33, 127–128 (1981); Higgs et al., Eur. Pharmacol. 66, 81–86 (1980) and Piper et al., Prostaglandins 19, 371 (1980)). There is a pressing need for compounds which do not process these undesirable side-effects.

Surprisingly, the sulphenamides which can be used according to the invention very specifically inhibit lipoxygenase even at those concentrations at which cyclooxygenase is not affected. This very strong and specific effect of the sulphenamides could not be expected from knowledge of the state of the art. The sulphenamides according to the invention which inhibit lipoxygenase can thus be used as medicaments for the treatment of inflammatory and allergic processes. They can be used, in particular, as antiphlogistic, antirheumatic, antiatherosclerotic, antiasthmatic, antiallergic, antimetastatic and gastro-protective agents.

According to the present invention there are provided pharmaceutical compositions containing as an active ingredient a compound which is a sulphenamide of the formula

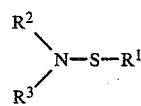 (I)

or a pharmaceutically acceptable acid addition salt thereof, in which $R^1$ represents an alkyl group with 1 to 18 carbon atoms, an alkenyl or alkinyl group with 2 to 12 carbon atoms, an aralkyl group with 7 to 12 carbon atoms which is mono- or bi-cyclic carbocyclic in the aryl portion and contains 1 or 2 carbon atoms in the alkyl portion, a cycloalkyl group with 5 to 8 (preferably 5 to 6) carbon atoms or an aryl group with 6 to 14 carbon atoms which is carbocyclic and preferably mono- or bi-cyclic, these radicals optionally being substituted by 1,2,3, 4 or 5 identical or different substituents selected from alkoxy, alkyl, aralkyl, cycloalkyl, aryl, aryloxy, arylthio, alkylthio, carboxyl, carbalkoxy, cyano, carbamoyl, sulphonyl, halogenoalkyl, halogenoalkoxy, halogen, amino and substituted amino, or represents an electron-attracting radical (preferably, independently of $R^2$ represent one of the preferred radicals mentioned below for $R^2$); or represents a radical of the formula $$-Q-S-NR^2R^{3'} \quad (Ia),$$

in which $R^2$ has the meaning given below, $R^{3'}$ independently of $R^3$ has the meaning given below for $R^3$, except a radical of formula (Ia), Q represents an alkylene radical with 1 to 12 carbon atoms which is optionally interrupted by one, two or more oxygen, sulphur or nitrogen atoms, or represents a cycloalkylene radical with 5 to 12 carbon atoms, an arylene radical with 6 to 10 carbon atoms, an alkylene-cycloalkylene-alkylene or alkylene-arylene-alkylene radical, or a bivalent heterocyclic ring, $R^2$ denotes an electron-attracting radical, preferably selected from;

(a) $-CO-R^4$ in which $R^4$ represents a hydrogen atom, an alkyl, cycloalkyl, alkenyl, aralkyl, aryl, alkoxy, aralkoxy, aryloxy, alkylthio, aralkylthio or arylthio group or a radical of the formula $-NR^3R^5$, in which $R^3$ has the meaning given below and $R^5$ denotes a hydrogen atom, independently of $R^1$, has any of those meanings given for $R^1$, or denotes a radical of the formula $$-W-CO-NR^{3''}R^{5'} \quad (Ib),$$

in which $R^{5'}$ has any of the meanings given for $R^5$, except a radical of formula (Ib), W represents a direct bond, a disulphide bridge or one of the bridge members mentioned above for Q, $R^{3''}$ independently of $R^3$, has any of those meanings given for $R^3$, other than $-NR^2R^5$, (b) a heterocyclic radical which has 5 to 8 ring members and contains 1 to 4 (preferably 1 or 2) heteroatoms selected from oxygen, sulphur and nitrogen, this heterocyclic radical being optionally fused with an aryl (preferably a monocyclic carboncyclic) radical and contains up to 5 (preferably 1 or 2) identical or different substituents selected from halogen, alkylthio, cycloalkylthio, aralkylthio, arylthio, alkoxy, aryloxy, cyano, nitro, cycloalkoxy, aralkoxy, $-NR^3R^5$, $-CO-R^4$, $-SO_2R^6$, $-SR^1$, trifluoromethyl, trifluoromethoxy, oxo, thiono,
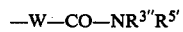

imino or substituted imino, substituents of the imino group being the radicals mentioned in the definition of $R^1$ or a carbamoyl radical, which carries a substituent on the nitrogen selected from alkyl, aryl and cycloalkyl, (c) $-SO_2-R^6$ in which $R^6$ represents a fluoroalkyl radical, one of the radicals mentioned in the definition of $R^4$ or a radical of the formula $$-W-SO_2-NR^3R^5, \qquad (Id)$$

in which $R^3$, $R^5$ and W have the meanings given above and below respectively, and $$\begin{array}{c} R^7 \\ | \\ -P=O \\ | \\ R^8 \end{array} \qquad (d)$$

wherein $R^7$ and $R^8$ are identical or different and in each case represent a group of the general formula $-NR^5-SR^1$, a hydrogen or halogen atom or an optionally substituted alkyl, alkenyl, cycloalkenyl, aryl, alkoxy, alkenoxy, cycloalkoxy, aryloxy, alkylthio, alkenylthio, cycloalkylthio, arylthio, heterocyclylthio or amino group, or $R^7$ and $R^8$ together with the phosphorus atom to which they are attached form a heterocyclic ring), and $R^3$ independently of $R^1$, has any of those meanings given for $R^1$, denotes a hydrogen atom or a radical of the general formula $-S-R^1$ or $-NR^2R^5$, in which $R^1$, $R^2$ and $R^5$ have the meanings given above, or $R^3$ together with $R^2$ forms a heterocyclic ring which is optionally fused with a benzene or heterocyclic ring and has 5 to 12 ring members, and which can contain 1 to 4 N atoms, 1 or 2 O atoms, 1 or 2 S atoms and is optionally substituted by alkyl, cycloalkyl, alkenyl, aralkyl, aryl, alkoxy, aryloxy, alkylmercapto, mercapto, amino, cyano, halogen, carbalkoxy, 1 to 3 oxo groups, 1 or 2 thiono groups and/or 1 or 2 optionally substituted imino groups, in admixture with an inert pharmaceutical carrier, i.e. a solid or liquid gaseous diluent, or in admixture with a liquid diluent other than a solvent of a molecular weight less than 200 except in the presence of a surface active agent.

As used herein and unless otherwise specified, the terms "alkoxy", "alkyl" and "alkylthio" contain 1 to 18, preferably 1 to 8, carbon atoms; the term "aralkyl" is mono- or bi-cyclic, carbocyclic in the aryl portion and contains 1 to 4 (preferably 1 to 2) carbon atoms in the alkyl portion; "cycloalkyl" contains 5 to 8 (preferably 5 to 6) carbon atoms; the terms "aryl", "aryloxy" and "arylthio" are preferably mono- or bi-cyclic carbocyclic aryl; the term "carboxyl" contains 1 to 8 (preferably 1 to 4) carbon atoms; the terms "halogenoalkyl" and "halogenoalkoxy" contain 1 to 4 carbon atoms and 1 to 5 halogen (preferably chlorine or fluorine) atoms; the term "halogen" is preferably chloro, bromo or fluoro; "substituted amino" is preferably alkyl-substituted amino containing 1 to 8 and preferably 1 to 4 carbon atoms in each alkyl group; the term "cycloalkylene" contains 1 to 12 (preferably 1 to 8) carbon atoms; the term "cycloalkylene" contains 5 to 12 (preferably 5 to 6) carbon atoms; the term "arylene" is preferably a mono- or bi-cyclic carbocylic arylene moiety.

Particularly preferred sulphenamides of the general formula (I) for use as active compound according to the present invention are those in which $R^1$ represents optionally substituted alkyl with 1 to 18 (especially 1 to 8) carbon atoms, a cycloalkyl group with 5 to 8 (especially 5 to 6) carbon atoms or an aryl group (especially a mono- or bi-cyclic carbocyclic aryl group with 6 to 14 carbon atoms, these radicals optionally being substituted by 1,2,3,4 or 5 identical or different substitutents selected from alkyl and alkoxy with in each case 1 to 4 carbon atoms, aralkyl with 7 to 12 carbon atoms (especially mono- or bi-cyclic carbocyclic aralkyl with 1 or 2 carbon atoms in the alkyl portion), cycloalkyl with 5 to 7 carbon atoms, phenyl, phenoxy, phenylthio, alkylthio with 1 to 4 carbon atoms, carboxyl carbalkoxy with 1 to 4 carbon atoms, cyano, trifluoromethyl, trifluoromethoxy, fluorine, chlorine, bromine, amino, benzyl-substituted amino and alkyl-substituted amino (the alkyl substituents(s)thereof carrying 1 to 4 carbon atoms), $R^2$ denotes an electron-attracting radical selected from (a) $-CO-R^4$, wherein $R^4$ represents a hydrogen atom, an alkyl group with 1 to 17 (especially 1 to 8) carbon atoms, a cycloalkyl group with 5 to 8 (especially 5 to 6) carbon atoms, an aralkyl group with 7 to 12 carbon atoms (especially mono- or bi-cyclic carbocyclic aralkyl with 1 or 2 carbon atoms in the alkyl portion), an aryl group with 6 or 10 carbon atoms (especially a mon- or bi-cyclic carbocyclic aryl group), an alkoxy group with 1 to 12 (especially 1 to 6) carbon atoms, an aralkoxy group with 7 to 10 carbon atoms (especially mono- or bi-cyclic carbocyclic aralkoxy with 1 to 2 carbon atoms in the alkoxy portion), an aryloxy group with 6 or 10 carbon atoms (especially a mono- bi-cyclic carbocyclic aryloxy group), an alkylthio group with 1 to 12 (especially 1 to 6) carbon atoms, a benzylthio group, an arylthio group with 6 or 10 carbon atoms (especially a mono- or bi-cyclic carbocylic arylthio group), or a radical of the formula $-NR^3R^5$, in which $R^3$ has the meaning given immediately below and $R^5$ denotes a hydrogen atom, independently of $R^1$, denotes one of the radicals mentioned immediately above for $R^1$, or denotes a radical of the formula $$-W-CO-NR^3R^{5'} \qquad (Ib')$$

in which $R^3$ has any of those meanings given immediately below, $R^{5'}$ has any of those meanings given immediately above for $R^5$ W represents a direct bond or a disulphide bridge, (b) a heterocyclic radical which has 5 to 8 ring members, and contains 1 to 4 hetero-atoms selected from oxygen, sulphur and nitrogen, this heterocyclic radical being optionally fused with an aryl radical with 6 to 14 carbon atoms and contain up to 5 identical or different substituents selected from the group comprising fluorine, chlorine, bromine, alkylthio with 1 to 4 carbon atoms, benzylthio, phenylthio, alkoxy with 1 to 4 carbon atoms, phenoxy, benzyloxy, one of the radicals mentioned under $R^1$, $-NR^3R^5$, $-CO-R^4$, trifluoromethyl, trifluoromethoxy, oxo and thiono and $R^3$ independently of $R^1$ and $R^2$ represents one of the radicals mentioned immediately above for $R^1$ or $R^2$, or denotes a hydrogen atom, —S—$R^1$ or —NH$R^2$, in which $R^1$ and $R^2$ have the meaning given immediately above, or $R^3$ together with $R^2$ forms a heterocyclic ring which is optionally fused with a benzene ring and has 5 to 12 ring members, and which contains 1 to 4 nitrogen atoms and optionally 1 or 2 oxygen atoms and 1 or 2 sulphur atoms, and is optionally substituted by alkyl with 1 to 4 carbon atoms, benzyl, aryl with 6 to 10 carbon atoms, alkoxy with 1 to 4 carbon atoms, phenoxy, alkylmercapto with 1 to 4 carbon atoms, amino, fluorine, chlorine, bromine, carbalkoxy with 1 to 4 carbon atoms, 1 to 3 oxo groups, 1 or 2 thiono groups and/or 1 or 2 imino groups.

The compounds of the formula (I) which can be used according to the present invention are known or are prepared by methods known from the literature, for example by reaction of a sulphenyl halide of the general formula $R^1$—S—X (II) with an amine of the formula Y—NR$^2$R$^3$ (III), X-Y being split off (see E. Kühle, The Chemistry of the Sulphenic Acids, Georg Thieme Verlag, Stuttgart 1973 page 83–91).

The radical X represents a chlorine, bromine or iodine atom, preferably a chlorine atom. The radical Y, which is split off by the reaction of the amine, preferably represents a hydrogen atom, a trialkylsilyl group, a metal such as K, Na, Li, Mg, Ca, Ba, Ag, Cu, Zn, Fe, Mn, Pb, Sn or Al, or an ammonium radical.

In the case where Y denotes a hydrogen atom, it is advantageous to carry out the reaction in the presence of a base. Preferred bases which may be mentioned are organic compounds such as triethylamine, tributylamine, benzyldimethylamine, dimethylaniline, pyridine or quinoline. The reaction is advantageously carried out in the presence of an aprotic solvent (such as hexane, petroleum ether, benzene, toluene, chlorobenzene, chloroform, carbon tetrachloride, dimethylsulphoxide or dimethylformamide).

In the case where Y does not represent a trialkylsilyl radical, it can be advantageous to carry out the preparation in an aqueous-organic two-phase medium. In this case, an inorganic base (such as an alkali metal or alkaline earth metal hydroxide or carbonate) can also be employed as removers of hydrogen halide.

The reaction can be carried out at a temperature between $-80°$ and $+150°$ C., preferably between $0°$ and $50°$ C.

Suitable amines of the general formula (III) for carrying out the invention are known or can be prepared by known methods (Literature: Houben-Weyl, Methoden der Organischen Chemie (Methods of Organic Chemistry), volume XI-2, 4th edition, G. Thieme Verlag, Stuttgart 1958, page 3 et seq.; Aminoheterocycles: see A. Weissberger, The Chemistry of Heterocyclic Compounds, Interscience, 1950-79; S. Coffey, Rodd's Chemistry of Carbon Compounds, 2nd edition, volume IV A-K, Elsevier Publ., Amsterdam—New York—London 1973-79).

Suitable sulphenyl halides of the general formula (II) for carrying out the invention are known or can also be prepared by known methods (see E. Kühle, The Chemistry of the Sulphenic Acids, G. Thieme Verlag, Stuttgart 1973, page 2-37).

The lipoxygenase-inhibitory properties of the sulphenamides are demonstrated by a method analogous to that of Bailey et al., J. Biol. Chem. 255, 5996, (1980) and according to R. H. Flower, Prostaglandins 16, 417 (1978). In this test method, the metabolism of radioactively labelled arachidonic acid by washed human platelets is investigated. In this in vitro test, the radioactively labelled metabolites are extracted from the reaction mixture and separated by thin layer chromatography. The autoradiogram is evaluated on the thin layer scanner. Under these test conditions, the labelled metabolites are separated from the unreacted arachidonic acid and can subsequently be quantitatively evaluated. The distribution of the radioactivity in the cyclooxygenase products, formed during metabolism, thomboxane B$_2$ (TXB$_2$) and 12-hydroxy-5,8,10-heptadecatrienic acid (HHT) and the lipoxygenase product 12-hydroxy-5,8,11,14-eicosatetraenoic acid (HETE) as influenced by the inhibitors, gives a measure of the inhibition of the enzymes.

The inhibition of lipoxygenase by the sulphenamides which can be used according to the invention can be measured by the inhibition of the synthesis of HETE. It is found that the synthesis of TXB$_2$ and of HHT remain unaffected, whilst the conversion of arachidonic acid decreases. As can be seen from the following table, the sulphenamides bring about a significant inhibition of the platelet lipoxygenase (synthesis of HETE). Inhibition of the platelet lipoxygenase (synthesis of HETE)

TABLE 1

| Inhibition of the platelet lipoxygenase (synthesis of HETE) | |
|---|---|
| Compound from Example No. | Minimum effective inhibitory concentration (g/ml) (at least 50% inhibition) |
| 2 | $10^{-6}$ |
| 3 | $10^{-6}$ |
| 17 | $3 \times 10^{-6}$ |
| 18 | $3 \times 10^{-6}$ |
| 19 | $10^{-6}$ |
| 23 | $10^{-6}$ |
| 24 | $10^{-6}$ |
| 25 | $10^{-6}$ |
| 29 | $10^{-6}$ |
| 30 | $3 \times 10^{-6}$ |
| 31 | $3 \times 10^{-6}$ |
| 32 | $3 \times 10^{-6}$ |
| 35 | $3 \times 10^{-6}$ |
| 39 | $10^{-6}$ |
| 40 | $3 \times 10^{-6}$ |
| 41 | $10^{-6}$ |
| 42 | $3 \times 10^{-6}$ |
| 43 | $3 \times 10^{-6}$ |
| 52 | $10^{-6}$ |
| 53 | $10^{-6}$ |
| 54 | $10^{-6}$ |
| 55 | $10^{-6}$ |
| 56 | $3 \times 10^{-6}$ |
| 57 | $10^{-5}$ |
| 60 | $3 \times 10^{-6}$ |
| 61 | $10^{-6}$ |
| 62 | $3 \times 10^{-6}$ |
| 68 | $3 \times 10^{-6}$ |
| 71 | $3 \times 10^{-6}$ |
| 72 | $10^{-6}$ |
| 73 | $10^{-6}$ |
| 74 | $10^{-6}$ |
| 75 | $3 \times 10^{-6}$ |
| 76 | $3 \times 10^{-6}$ |
| 80 | $10^5$ |
| 84 | $10^5$ |

The sulphenamides used according to the present invention are also active in vivo. This activity is demonstrated by the measurement of the inhibition of the migration of leucocytes by methods which are in themselves known (see Higgs et al., Biochemical Pharmacology 28, 1959, (1979) and Eur. J. Pharmacol. 66, 81 (1980)). Table 2 which follows summarises the activities of some illustrative sulphenamides after local administration, by introduction of a piece of sponge soaked in the active compound under the dorsal skin of rats.

TABLE 2

| Compound No. | Dose, Local (mg/rat) | Inhibition of the migration of leucocytes (control = 0%) |
|---|---|---|
| 2 | 10 | 70% |
| 4 | 10 | 61% |
| 5 | 10 | 22% |
| 10 | 10 | 26% |
| 11 | 10 | 22% |
| 15 | 10 | 47% |
| 16 | 10 | 40% |
| 18 | 10 | 41% |
| 19 | 10 | 60% |
| 20 | 10 | 64% |
| 21 | 10 | 44% |
| 22 | 10 | 64% |
| 29 | 10 | 48% |
| 31 | 10 | 43% |
| 32 | 10 | 38% |
| 36 | 10 | 64% |
| 38 | 10 | 56% |
| 40 | 10 | 41% |
| 45 | 10 | 40% |
| 47 | 10 | 21% |
| 52 | 10 | 76% |
| 55 | 10 | 78% |
| 56 | 10 | 86% |
| 58 | 10 | 78% |
| 69 | 10 | 20% |
| 71 | 10 | 65% |
| 74 | 10 | 52% |

The antiasthmatic activity of the compound used according to the present invention can also be detected by methods which are already known (see Samuelson et al., FEBS Letters, 110, 213 (1980) and Yet et al., Agents and Actions 10, 274 (1980)).

As stated above, the invention also relates to the use in medicine for combating inflammatory or allergic processes, of the compounds of the invention.

The present invention provides a pharmaceutical composition containing as active ingredient a compound of the invention in admixture with an inert pharmaceutical carrier, i.e. a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical composition according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granules) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) absorptive carriers, e.g. kaolin and bentonite; (i) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters (e.g. $C_{14}$-alcohol with $C_{16}$-fatty acid)) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example ground nut oil), glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.5 to 90% of the active ingredient by weight of the total composition.

In addition to a compound of the invention, the pharmaceutical compositions and medicaments according to this invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for intravenous administration of the medicaments of the invention is 2.5 mg to 250 mg of active ingredient, and for oral administration is 5 mg to 500 mg of active ingredient.

The production of the above-mentioned pharmaceutical compositions and medicaments is carried out by any method known in the art, for example, by mixing the active ingredient(s) with the diluent(s) to form a pharmaceutical composition (e.g. a granule) and then forming the composition into the medicament (e.g. tablets).

This invention further provides a method of combating the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), rectally or locally, preferably orally or parenterally, especially perlingually or intravenously. Preferred pharmaceutical compositions and medicaments are therefore those adapted for administration such as oral or parenteral administration. Administration in the method of the invention is preferably oral or parenteral administration.

In general it has provided advantageous to administer intravenously amounts of from 0.01 to 10 mg/kg, preferably from 0.05 to 5 mg/kg, of body weight per day or to administer orally 0.05 to 100 mg/kg, preferably 0.01 to 10 mg/kg, of body weight per day, to achieve effective results. Nevertheless, it can at times be necessary to deviate from those dosage rates, and in particular to do so as a function of the nature and body weight of the subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

The following Examples illustrate the production of the active ingredients use according to the present invention in more detail:

EXAMPLE 1

A solution of 0.5 mol of trichloromethylsulphenyl chloride in 300 ml of methylenchlorid was added dropwise to a suspension of 47.5 g (0.5 mol) of 2-pyrimidineamine and 44 g of pyridine in 300 ml of dry methylenchloride. The mixture was stirred for 6 hours at room temperature, and the mother liquor was filtered from the precipitated pyridine hydrochloride and extracted twice by shaking with ice-water. The organic phase was dried over sodium sulphate, the solvent was evaporated off in vacuo and the residue was recrystallised from toluene. 16 g of N-2-pyrimidine-trichloromethylsulphenamide were obtained as white crystals of melting point 178° to 179° C.

EXAMPLES 2–78

The compounds of the following Examples were obtained analogously to Example 1, as indicated in Table 3. In some cases, the sulphenamides obtained were sparingly soluble, so that they could be isolated by filtering off and washing with ice-water.

TABLE 3

$$R^2 \diagdown N-S-R^1$$
$$R^3 \diagup$$

| Example | —NR²R³ | —R¹ | Solvent used | Yield (%) | Melting point (°C.) (recrystallised from) (1) | Remarks |
|---|---|---|---|---|---|---|
| 2 | 3-Amino-1,2,4-triazolyl | Phenyl | Toluene/DMF | 61 | 154° C. (EE) | |
| 3 | " | 4-Chlorophenyl | " | 46 | 154–6° C. (EE) | Formed by crystallisation from Example 10 |
| 4 | " | 4-Methylphenyl | " | 43 | 130–2° C. | |
| 5 | 5-(Morpholin-4-yl)-1,3,4-thiadiazol-2-yl-NH | 4-Chlorophenyl | Toluene/DMF | 94 | 143–5 | |
| 6 | 5-Phenoxymethyl-oxazolidin-2-on-3-yl | " | " | 33 | 98–101 | |
| 7 | 3a,4,5,6,7,7a-Hexahydrobenzoxazolin-2-on-3-yl | " | " | 92 | viscous yellow oil | |
| 8 | 3-Phenyl-1,2,4-thiadiazol-5-yl-NH | 1-Phenyl-tetrazol-5-yl | Chlorobenzene/ dimethylacetamide | 37 | 154 | |
| 9 | 4-Phenylthiazol-2-yl-NH | 1-Phenyl-tetrazol-5-yl | Chlorobenzene/ dimethylacetamide | 40 | 152 | |
| 10 | Benzyl-NH— | 1-Phenyl-tetrazol-5-yl | Chlorobenzene/ dimethylacetamide | 62 | 46 | |
| 11 | 1,2,4-Triazol-3-yl-NH | 1-Phenyl-tetrazol-5-yl | Chlorobenzene/ dimethylacetamide | 35 | 175 | |
| 12 | " | Benzothiazol-2-yl | Chlorobenzene/ dimethylacetamide | 15 | 177° | |
| 13 | N—Acethyl-4-ethoxyaniline | 4-Chlorophenyl | Toluene/DMF | 73 | clear yellow oil | |
| 14 | N—Acetyl-4- | 4-Chlorophenyl | Toluene/DMF | 68 | light brown oil | |
| 15 | 2,2,5,5-Tetramethyloxazolidin-4-on-3-yl | " | " | 53 | 61–4° C. | |
| 16 | 2,2,5,5-Tetramethyloxazolidin-4-on-3-yl | 4-Methylphenyl | Toluene/DMF | 74 | brown oil | Crystallised completely after standing for a relatively long time |
| 17 | d-Benzolazin-2,6-dion-3-yl | " | Toluene/DMF | 81 | 190 (decomposition) | |
| 18 | Triazol[1,2-a]-triazol-1,3,5,7-tetraon-2,6-diyl | Phenyl | " | 45 | 143 (decomposition) (Tol) | Still contains some mono-sulphenylated product |
| 19 | Tert.-butylcarbamoyl | " | THF | 33 | 103 | Purified by column chromatography |
| 20 | N—Pyrrolidonyl | 4-Chloro-3-trifluoromethylphenyl | Chlorobenzene//DMF | 42 | 78–80 | |
| 21 | N—Pyrrolidonyl | 2-Chloro-5-trifluoromethylphenyl | Toluene/DMF | 45 | 97–100 | |
| 22 | N—Pyrrolidonyl | 4-Carbomethoxyphenyl | Toluene/DMF | 50 | 76–8 | Crystallised after trituration with cyclohexane |
| 23 | N—Phenylthio-2-chlorophenyl-carbamoyl | Phenyl | THF | 32 | 113–5 (ethanol) | |
| 24 | 2-Chlorophenyl-carbamoyl | Phenyl | THF | 3 | 116–8 (TOL) | Isolated from the mother liquor of Example 104 |
| 25 | Chloromethyl- | Phenyl | THF | 29 | 95–7 | |

TABLE 3-continued $$\begin{array}{c} R^2 \\ \phantom{R^2}\diagdown \\ \phantom{R^2\diagdown}N{-}S{-}R^1 \\ \phantom{R^2\diagdown N}\diagup \\ R^3 \end{array}$$

| Example | —NR²R³ | —R¹ | Solvent used | Yield (%) | Melting point (°C.) (recrystallised from) (1) | Remarks |
|---|---|---|---|---|---|---|
| 26 | 6-Carbomethoxy-1,3-thiazin-4-on-2-yl-NH carbamoyl | 4-Chlorophenyl | Toluene/DMF | 98 | (TOL) 165–8 | |
| 27 | 2-Benzothiazolyl | Phenyl | " | 19 | 150–4 (EE) | |
| 28 | 6-Methoxy-2-benzothiazolyl | Phenyl | " | 82 | 165–6 (EE) | |
| 29 | Phthalimidyl | Phenyl | " | 92 | 153–8 | |
| 30 | Phthalimidyl | 4-Chlorophenyl | Toluene/DMF | 77 | 163–5 | |
| 31 | " | 4-Methylphenyl | " | 77 | 190–2 | |
| 32 | " | Cyclohexyl | Toluene/acetone | 77 | 85–7 (WB) | |
| 33 | " | Isopropyl | Hexane/DMF | 32 | 63–5 (WB) | |
| 34 | " | 2-Carbomethoxyphenyl | Toluene/DMF | 77 | 244–6 | |
| 35 | " | 4-Tert.-butyl-phenyl | " | 55 | 155–7 | |
| 36 | 5-Nitrophthalimidyl | Phenyl | " | 81 | 136–8 | |
| 37 | " | 4-Tert.-butylphenyl | " | 40 | 146–8 | |
| 38 | " | 4-Chlorophenyl | Chlorobenzene/DMF | 44 | 181–3 (EE) | |
| 39 | 4-Nitrophthalimidyl | Phenyl | Toluene/DMF | 80 | 149–54 | |
| 40 | " | 4-Chlorophenyl | Chlorobenzene/DMF | 71 | 160–7 | |
| 41 | " | 4-Tert. | Toluene/DMF | 61 | 136–7 | |
| 42 | Tetrachlorophthalimidyl | Phenyl | Toluene/DMF | 65 | 207 | |
| 43 | " | 4-Tert.-butylphenyl | " | 54 | | |
| 44 | " | 4-Chloro- | " | 24 | 227–31 (Tol) | |
| 45 | 1,2,4,5-Benzenetetracarboxylic acid diimide-N,N'—diyl | Phenyl | " | 64 | 238 | |
| 46 | 1,2,4,5-Benzenetetracarboxylic acid diimide-N,N'—diyl | 4-Chlorophenyl | Chlorobenzene/DMF | 59 | 238–40 | |
| 47 | N—Naphthalimidyl | Phenyl | Toluene/DMF | 94 | 205–12 | |
| 48 | " | 4-Chlorophenyl | Chlorobenzene/DMF | 84 | 191–3 | |
| 49 | " | 4-Tert.-butylphenyl | Toluene/DMF | 69 | 196–8 | |
| 50 | N—Phthalimidyl | Benzoylmethyl | Chlorobenzene | 78 | 144–7 (WB) | |
| 51 | " | 2-Acetyl-2-propyl | " | 86 | 101–6 (Cy) | |
| 52 | N—Pyrrolidonly | Phenyl | Toluene/DMF | 81 | | |
| 53 | N—Pyrrolidonyl | 4-Chlorophenyl | Chlorobenzene/DMF | 46 | 78–80 (Cy) | |
| 54 | " | 4-Tert.-butylphenyl | " | 94 | Oil | |
| 55 | Hexahydroazepin-2-on-1-yl | Phenyl | Toluene/DMF | 38 | 63–8 | |
| 56 | Hexahydroazepin-2-on-1-yl | 4-Chlorophenyl | " | 64 | 79–81 (WB) | |
| 57 | Hexahydroazepin-2-on-1-yl | 4-Tert.-butylphenyl | " | 58 | 76–80 | |
| 58 | 2-Oxo-azacyclododecanyl | Phenyl | Toluene/DMF | 59 | Oil | |
| 59 | Phenylcarbamoyl | Phenyl | THF | 23 | 122–4 (Tol) | |
| 60 | N—Saccharinyl | Phenyl | Chlorobenzene | 91 | 139–41 | |
| 61 | " | 4-Chlorophenyl | " | 69 | 202 | |
| 62 | " | 4-Tert.-butylphenyl | " | 87 | 143 | |
| 63 | " | 2-Nitrophenyl | " | 62 | 170 | |

TABLE 3-continued $$R^2\diagdown N-S-R^1$$
$$R^3\diagup$$

| Example | —NR²R³ | —R¹ | Solvent used | Yield (%) | Melting point (°C.) (recrystallised from) (1) | Remarks |
|---|---|---|---|---|---|---|
| 64 | " | 2-Formyl-2-propyl | " | 83 | 133–5 | |
| 65 | 5,5-Dimethyl-hydantoin-1,3-diyl | Phenyl | Toluene/DMF | 26 | 104 | |
| 66 | 5,5-Dimethyl-hydantoin-1,3-diyl | 4-Tert.-butylphenyl | " | 66 | 140–2 (Cy/Tol) | |
| 67 | N—Isatinyl | Cyclohexyl | Dichloroethane/DMF | 75 | 101–4 | |
| 68 | " | Phenyl | Chlorobenzene/DMF | 66 | 118–23 | |
| 69 | " | 4-Chlorophenyl | " | 93 | 180–2 | |
| 70 | " | 4-Tert.-butylphenyl | " | 63 | 112–5 | |
| 71 | 1-(Phenylcarbonatimino)-isoindolin-3-on-2-yl | Phenyl | Toluene/DMF | 66 | 133–50 | |
| 72 | 1-Phenyl-pyrazolidin-3-on-2-yl | 4-Chlorophenyl | Chlorobenzene/DMF | 14 | 194–7 (Tol) | |
| 73 | 1-Phenyl-pyrazolidin-3-on-2-yl | 4-Tert.-butylphenyl | " | 12 | 170–2 (Cy/Tol) | |
| 74 | 4,5-Dihydro-3-methyl-pyrazol-5-on-1-yl | Phenyl | Toluene/DMF | 55 | 290 | |
| 75 | 1-Pyrazolyl | 4-Chlorophenyl | " | 65 | Oil | |
| 76 | e-Benzoxazin-2,4-dion-3-yl | Cyclohexyl | Pentane/DMF | 72 | 105–8 (iPr) | |
| 77 | 3-Methyl-1,2,4-thiadiazol-5-yl-NH | 4-Chloro-3-trifluoromethylphenyl | Toluene/DMF | 30 | 123–7 | Washed several times with petroleum ether |
| 78 | 5-Methyl-1,3,4-thiadiazol-2-yl-NH | 4-Fluorophenyl | " | 50 | 132–4 (Cy/Tol) | |

Abbreviations used in Table 3 for recrystallisation solvent "1)".
Cy=cyclohexane
EE=ethyl acetate
iPr=isopropanol
Me=methanol
Tol=toluene
WB=petroleum ether (with boiling point 100° to 140° C.).

EXAMPLES 79

42.5 g (0.5 mol) of 5-aminotetrazole were dissolved in 100 ml of water and 20 g (0.5 mol) of sodium hydroxide solution. 100 ml of chlorobenzene were added and a solution of 0.5 mol of trichloromethylsulphenyl chloride in 400 ml of chlorobenzene was then slowly added dropwise at +10° C. When the addition was complete the mixture was stirred for 30 minutes and then filtered. The residue was washed with petroleum ether and then dried over P₄O₁₀. 66% of theory of N-5-tetrazolyl-trichloromethylsulphenamide of melting point 117° to 118° C. (decomposition) were obtained.

EXAMPLE 80

NH₃ gas was passed into 80.4 g of trimethylchlorosilane in 500 ml of dry toluene at 50° to 60° C. to saturation. 59.1 g of benzimidazole were then added and the mixture was boiled for 10 hours under reflux. To remove excess ammonia, 250 ml of toluene were distilled off in vacuo, and 0.5 mol of cyclohexylsulphenyl chloride in 500 ml of pentane was then added dropwise. The mixture was subsequently stirred for 4 hours and filtered, and the solvent was removed in vacuo. 99 g of 1-cyclohexylthiobenzimidazole were obtained as a red-brown oil.

The Examples 81 to 86 were also obtained analogously to Example 80, as indicated in Table 4.

TABLE 4

$R^2R^3N-S-R^1$

| Example | —NR²R³ | —R¹ | Solvent | Yield (%) | Melting point (°C.) | Remarks |
|---|---|---|---|---|---|---|
| 81 | 1-Benzimidazolyl | Phenyl | Dichloroethane/toluene | 56 | 50–4 | Crystals precipitated after 2 weeks, washed with petroleum |

TABLE 4-continued $R^2R^3N-S-R^1$

| Example | $-NR^2R^3$ | $-R^1$ | Solvent | Yield (%) | Melting point (°C.) | Remarks |
|---|---|---|---|---|---|---|
| | | | | | | ether |
| 82 | " | Isopropyl | " | 65 | Oil | |
| 83 | " | n-Octyl | " | 92 | Oil | |
| 84 | " | Sec.-butyl | Pentane/toluene | 49 | Bp$_{0.1}$ 115–120° C. (yellow oil) | |
| 85 | 1-Imidazolyl | Cyclohexyl | " | 72 | yellow oil | By-product dicyclohexyl-disulphide was removed at 0.3 mbar and 70° C. bath temperature |
| 86 | " | n-Octyl | " | 90 | yellow oil | |

What is claimed is:

1. A pharmaceutical composition containing as an active ingredient a lipoxygenase-inhibiting amount of a compound which is a sulphenamide of the formula

or a salt thereof, in which represents an alkyl group with 1 to 18 carbon atoms, an alkenyl or alkinyl group with 2 to 12 carbon atoms, an aralkyl group with 7 to 11 carbon atoms, a cycloalkyl group with 5 to 8 carbon atoms or an aryl group with 6 to 14 carbon atoms, these radicals being optionally substituted with up to 5 identical or different substituents selected from alkoxy, alkyl, aralkyl, cycloalkyl, aryl, aryloxy, arylthio, alkylthio, carboxyl, carbalkoxy, cyano, carbamoyl, sulphonyl, halogenoalkyl, halogenoalkoxy, halogen, amino or substituted amino; independently of $R^2$, has any of the meanings of $R^2$; or represents a radical of the formula $$-Q-S-NR^2R^{3'} \quad (Ia)$$

in which $R^2$ has the meaning given below, $R^{3'}$ independently of $R^3$ has the meaning given below for $R^3$, except a radical of formula (Ia), Q represents an alkylene radical with 1 to 12 carbon atoms which is optionally interrupted by one or more oxygen, sulphur or nitrogen atoms, or represents a cycloalkylene radical with 5 to 12 carbon atoms, an arylene radical with 6 to 10 carbon atoms, an alkylene-cycloalkylene-alkylene or alkylene-arylene-alkylene radical, $R^2$ denotes an electron-attracting radical, and $R^3$ independently of $R^1$, has any of those meanings given for $R^1$, denotes a hydrogen atom or a radical of the general formula $-SR^1$ or $-NR^2R^5$, in which $R^5$ denotes a hydrogen atom, independently of $R^1$, has any of those meanings given for $R^1$, or denotes a radical of the general formula $$-W-CO-NR^{3''}R^{5'} \quad (Ib)$$

in which $R^{3''}$ independently of $R^3$, has any of those meanings given for $R^3$, other than $-NR^2R^5$, $R^{5'}$ has any of those meanings given for $R^5$ except a radical of formula (Ib), W represents a direct bond, a disulphide bridge or one of the bridge members mentioned above for Q, and $R^1$ and $R^2$ have the meaning mentioned above, or $R^3$ together with $R^2$ forms a tetrazolyl ring and is optionally substituted by alkyl, cycloalkyl, alkenyl, aralkyl, aryl, alkoxy, aryloxy, alkylmercapto, mercapto, amino, cyano, halogen, carbalkoxy, 1 to 3 oxo groups, 1 or 2 thiono groups and/or 1 or 2 optionally substituted imino groups, in admixture with an inert pharmaceutical carrier.

2. A composition according to claim 1 in which the active ingredient is a compound as defined in claim 1, in which $R^2$ denotes an electron-attracting radical selected from (a) $-CO-R^4$, in which $R^4$ represents a hydrogen atom, an alkyl, cycloalkyl, alkenyl, aralkyl, aryl, alkoxy, aralkoxy, aryloxy, alkylthio, aralkylthio or arylthio group or a radical of the general formula $-NR^3R^5$, in which $R^3$ and $R^5$ have the same meanings as in claim 1, (b) or a carbamoyl radical, which carries a substituent on the nitrogen selected from alkyl, aryl and cycloalkyl, (c) $SO_2-R^6$, in which $R^6$ represents a fluoroalkyl group, one of the radicals listed above for $R^4$ or a radical of the general formula $-W-SO_2-NR^3R^5$, in which $R^3$, $R^5$ and W have the same meanings as in claim 1, and

(d)

in which $R^7$ and $R^8$ are identical or different and in each case represent a group of the general formula $-NR^5-SR^1$, a hydrogen or halogen atom or an optionally substituted alkyl, alkenyl, cycloalkenyl, aryl, alkoxy, alkenoxy, cycloalkoxy, aryloxy, alkylthio, alkenylthio, cycloalkylthio, arylthio, heterocyclylthio or amino group.

3. A composition according to claim 1 in which the active ingredient is a compound as defined in claim 1, in which $R^1$ has any of the meanings given in claim 1, except an electron-attracting radical.

4. A composition according to claim 1 in which the active ingredient is a compound as defined in claim 1, in which $R^1$ represents an optionally substituted alkyl group with 1 to 18 carbon atoms, a cycloalkyl group with 5 to 8 carbon atoms or an aryl group with 6 to 14 carbon atoms, these radicals optionally being substituted by up to 5 identical or different substituents selected from alkyl and alkoxy with in each case 1 to 4 carbon atoms, aralkyl with 7 to 10 carbon atoms, cycloalkyl with 5 to 7 carbon atoms, phenyl, phenoxy, phenylthio, alkylthio with 1 to 4 carbon atoms, carboxyl, carbalkoxy with 1 to 4 carbon atoms, cyano, trifluoromethyl, trifluoromethoxy, fluorine, chlorine, bromine, amino, benzyl-substituted amino and alkyl-substituted amino, (the alkyl substituent(s) thereof carrying 1 to 4 carbon atoms), $R^2$ denotes an electron-attracting radical selected from (a) $-CO-R^4$, in which $R^4$ represents a hydrogen, alkyl with 1 to 17 carbon atoms, cycloalkyl with 5 to 8 carbon atoms, aralkyl with 7 to 10 carbon atoms, aryl with 6 or 10 carbon atoms, alkoxy with 1 to 12 carbon atoms, aralkoxy with 7 to 10 carbon atoms, aryloxy with 6 or 10 carbon atoms, alkylthio with 1 to 12 carbon atoms, benzylthio, arylthio with 6 or 10 carbon atoms or a radical of the general formula $-NR^3R^5$, in which $R^3$ has the meaning given immediately below and $R^5$ denotes a hydrogen atom, independently of $R^1$ denotes one of the radicals mentioned under $R^1$ immediately above, or denotes a radical of the general formula $-W-CO-NR^3-R^{5'}$ (Ib')

in which $R^3$ has any of those meanings given immediately below, $R^{5'}$ has any of those meanings given for $R^5$ except a radical of formula Ib'), and W is as defined in claim 1

$R^3$ independently of $R^1$ and $R^2$ represents one of the radicals mentioned immediately above for $R^1$ and $R^2$, or denotes a hydrogen atom, $-S-R^1$ or $-NHR^2$, in which $R^1$ and $R^2$ have the meanings given immediately above, or $R^3$ together with $R^2$ forms a tetrazolyl ring which is optionally fused with a benzene ring and has 5 to 12 ring members, and which contains 1 to 4 nitrogen atoms and optionally 1 or 2 oxygen atoms or 1 or 2 sulphur atoms, and is optionally substituted by alkyl with 1 to 4 carbon atoms, benzyl, aryl with 6 or 10 carbon atoms, alkoxy with 1 to 4 carbon atoms, phenoxy, alkylmercapto with 1 to 4 carbon atoms, amino, fluorine, chlorine, bromine, carbalkoxy with 1 to 4 carbon atoms, 1 to 3 oxo groups, 1 or 2 thiono groups and/or 1 or 2 imino groups.

5. A composition according to claim 1 in which $R^1$ is 1-phenyltetrazol-5-yl and $-NR_2R_3$ is benzyl$-NH-$.

6. A pharmaceutical composition of claim 1 containing as an active ingredient a compound as defined in any of claims 1, 2 and 6 in the form of a sterile or physiologically isotonic aqueous solution.

7. A composition according to claims 1, 2 or 6 containing 0.5 to 95% of active ingredient, by weight.

8. A medicament in dosage unit form comprising a lipoxygenase-inhibiting amount of a compound as defined in claim 1 either alone or in admixture with a diluent.

9. A medicament of claim 14 in the form of tablets, pills, dragees, capsules, ampoules, or suppositories.

10. A method of combating inflammatory or allergic or arthritic or ashmatic processes in warm-blooded animals which comprises administering to the animals a compound as defined in claim 1 either alone or in admixture with a diluent or in the form of a medicament.

11. A method according to claim 10 in which the active compound is administered intraveneously in an amount of 0.01 to 10 mg per kg body weight per day.

12. A method according to claim 10 in which the active compound is administered orally in an amount of 0.05 to 100 mg per kg body weight per day.

* * * * *

UNITED STATES PATENT AND TRADEMARK OFFICE
CERTIFICATE OF CORRECTION

PATENT NO. : 4,447,440

DATED : May 8, 1984

INVENTOR(S) : Wolf-Dieter Busse et al.

It is certified that error appears in the above-identified patent and that said Letters Patent is hereby corrected as shown below:

| | |
|---|---|
| Col. 2, lines 64, 65 and Col. 4, line 10 | Delete "substitutents" and substitute --substituents-- |
| Col. 3, line 68, Col. 4, line 38 and Col. 4, line 42 | Delete "carbocylic" and substitute --carbocyclic-- |
| Col. 4, line 32 | Delete "mon-" and substitute --mono- -- |
| Col. 10, line 15 | Delete "provided" and substitute --proved-- |
| Col. 10, line 46 | Delete "methylenchlorid" and substitute --methylenechloride-- |
| Col. 11, Ex. 13, 2nd Col. | Delete "Acethyl" and substitute --Acetyl-- |
| Col. 11, Ex. 17, 2nd Col. | Delete "d-Benzolazin-" and substitute --d-Benzoxazin- -- |
| Col. 13, Ex. 41, 3rd Col. | After "4-Tert.-" insert --butylphenyl-- |
| Col. 13, Ex. 44, 3rd Col. | After "4-Chloro-" insert --phenyl-- |
| Col. 17, line 29 | Before "represents" insert --$R^1$-- |
| Col. 18, line 25 | After "ring" delete "and" and substitute --which-- |

Signed and Sealed this

Eighth Day of January 1985

[SEAL]

Attest:

*Attesting Officer*

GERALD J. MOSSINGHOFF

*Commissioner of Patents and Trademarks*